United States Patent [19]

Klose

[11] 4,141,938
[45] Feb. 27, 1979

[54] PRODUCTION OF ACID ORTHOPHOSPHORIC ACID ESTER MIXTURES

[75] Inventor: Werner Klose, Erftstadt Liblar, Fed. Rep. of Germany

[73] Assignee: Hoechst Aktiengesellschaft, Frankfurt am Main, Fed. Rep. of Germany

[21] Appl. No.: 851,944

[22] Filed: Nov. 16, 1977

Related U.S. Application Data

[63] Continuation-in-part of Ser. No. 838,464, Oct. 3, 1977, abandoned.

[30] Foreign Application Priority Data

Oct. 7, 1976 [DE] Fed. Rep. of Germany ....... 2645211

[51] Int. Cl.$^2$ .............................................. C07F 9/09
[52] U.S. Cl. .................................... 260/928; 260/980
[58] Field of Search ............................... 260/980, 928

[56] References Cited

U.S. PATENT DOCUMENTS

| | | | |
|---|---|---|---|
| 2,510,033 | 5/1950 | Kyrides | 260/980 X |
| 3,276,916 | 10/1966 | Wurstner | 260/980 X |
| 3,407,150 | 10/1968 | Wismer et al. | 260/980 X |

*Primary Examiner*—Anton H. Sutto
*Attorney, Agent, or Firm*—Connolly and Hutz

[57] ABSTRACT

Orthophosphoric acid esters are made by reacting phosphorus(V)-oxide with an alcoholic component. More specifically, phosphorus(V)-oxide is reacted by mixing or kneading it with a blend consisting of a monohydric alcohol and an alkane polyol containing 2 to 12 carbon atoms and 2 to 6 hydroxyl groups, at approximately 0 to 120° C. with the exclusion of moisture, in the presence of an inert gas, and over a period of approximately 1 to 6 hours. The resulting reaction product is cooled.

12 Claims, No Drawings

PRODUCTION OF ACID ORTHOPHOSPHORIC ACID ESTER MIXTURES

This application is a continuation-in-part application of application Ser. No. 838,464 filed Oct. 3, 1977, abandoned by Werner Klose.

This invention relates to the production of a mixture of acid orthophosphoric acid esters from phosphorus(V)-oxide and a blend of a monohydric alkanol and an alkane polyol.

Various processes for making acid phosphoric acid esters have already been disclosed. Thus, for example, it is possible to prepare these compounds by subjecting phosphorus oxychloride to a partial reaction with an organic hydroxyl compound and by subjecting the resulting phosphoric acid ester chloride to hydrolyses. This, however, is a commercially unattractive procedure inasmuch as the acid esters are difficult to separate from the aqueous solution.

Of more interest is the reaction of phosphorus(V)-oxide with an organic hydroxyl compound, in which a mixture of orthophosphoric acid mono- and diesters is obtained from phosphorus(V)-oxide and a compound of the formula ROH, in accordance with the following equation (I):

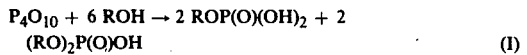

$$P_4O_{10} + 6 ROH \rightarrow 2 ROP(O)(OH)_2 + 2 (RO)_2P(O)OH \qquad (I)$$

A special process for making a mixture of orthophosphoric acid esters has been disclosed in German Patent Specification No. 1,226,101. This prior process for making a mixture of orthophosphoric acid mono- and diesters from phosphorus(V)-oxide and an alkanol or phenol comprises reacting phosphorus(V)-oxide with a blend of the orthophosphoric acid mono- and diesters of the respective alcohol or phenol in a molar ratio smaller than 1:2, preferably 1:3 to 1:6, and further reacting the resulting acid phosphoric acid esters with a quantity of the alcohol or phenol corresponding to the quantity of phosphorus(V)-oxide and to the composition desired for the ester mixture, the two reaction stages being effected at temperatures of 20 to 100° C.

The alcoholic components which are used in this known process include, for example, methanol, ethanol, cyclohexanol, phenol, ethylene glycol or butane diol. In other words, the alcoholic compound used in each particular case is a homogeneous compound. If use is made of an alkanol, the reaction product accordingly is a mixture of phosphoric acid mono- and diesters, and if use is made of an alkane diol, the reaction product is a mixture of the phosphoric acid mono- and diesters of the alkane diol.

We have now unexpectedly found that the reaction of phosphorus(V)-oxide does not exclusively produce the above phosphoric acid mono- and diesters of the respective alcohol, but also a reaction mixture containing a considerable proportion of acid alkane polyol phosphoric acid esters which are esterified with the monohydric alcohol.

The present invention relates more specifically to a process for making a mixture of orthophosphoric acid esters by reacting phosphorus(V)-oxide with an alcoholic component which comprises: reacting phosphorus(V)-oxide by mixing or kneading it with a blend consisting of a monohydric alcohol and an alkane polyol containing 2 to 12 carbon atoms and 2 to 6 hydroxyl groups, in a molar matio of phosphorus(V)-oxide to monohydric alcohol to alkane polyol of 1 to 2 to 4/n, in which n stands for the number of hydroxyl groups present in the alkane polyol molecule, the reaction being effected at approximately 0° to 120° C. with the exclusion of moisture, in the presence of an inert gas, and over a period of approximately 1 to 6 hours; and cooling the resulting reaction product.

In a preferred version of the present process, the monohydric alcohol is an aliphatic alcohol having 1 to 22 carbon atoms, or the product which is obtained by reacting an aliphatic alcohol having 1 to 22 carbon atoms or a phenol having 6 to 18 carbon atoms with 2 to 20 mols of ethylene oxide. The alcohols which can be used comprise more specifically, for example: methanol, ethanol, isopropanol, n-butanol, isobutanol, cyclohexanol, 2-ethylhexanol, lauryl alcohol, isotridecyl alcohol, stearyl alcohol, oleyl alcohol; a commercial mixture of aliphatic alcohols, 2-chloroethanol, 2,3-dibromopropanol-1; 3-methoxybutanol-1or 2-phenylpropanol-1, and also the ethylene oxide addition products of methyl glycol, ethyl glycol, butyl glycol or butyl diglycol; or the addition products of 4 moles of ethylene oxide and 1 mol of lauryl alcohol, of 8 mols of ethylene oxide and 1 mol of stearyl alcohol, of 6 mols of ethylene oxide and 1 mol of phenol, or of 8 mols of ethylene oxide and 1 mol of nonyl phenol.

The alkane polyol components, which may preferably be used comprise: ethylene glycol; propane diol-1,2; propane diol-1,3; butane diol-1,3; butane diol-1,4; diethylene glycol; polyethylene glycol; neopentyl glycol; dibromoneopentyl glycol; glycerol; trimethylolpropane; mannitol or pentaerythritol.

Depending on the number of hydroxyl groups which are present per molecule of alkane polyol, the reactants are used in certain molar ratios. Where a monohydric alcohol is used, it is preferable to use phosphorus(V)-oxide, monohydric alcohol and alkane diol in a molar ratio of 1:2,2, and where an alkane tetrol is used as the alkane polyol, it is preferable to use a molar ratio of 1:2:1.

It has finally been found advantageous to effect the reaction of phosphorus(V)-oxide with the monohydric alcohol and alkane polyol during the strongly exothermal phase at temperatures of 0° to 60° C., preferably 20° to 40° C., by cooling the reaction mixture, and to effect the end phase of the reaction at temperatures of 80° to 100° C. by heating the reaction mixture. It is also good practice to effect the reaction in the presence of an inert gas, e.g. nitrogen. The reaction is generally terminated after 1 to 3 hours, after which period reaction heat which is evolved during the initially strongly exothermal reaction phase, ceases to be evolved.

The ester mixture obtainable by the present process has not been obtained heretofore. In view of this, the invention is also directed to a novel acid orthophosphoric acid ester mixture which is obtained by reacting phosphorus(V)-oxide by mixing or kneading it with a blend consisting of, and containing, a monohydric alcohol and an alkane polyol containing 2 to 12 carbon atoms and 2 to 6 hydroxyl groups, in a molar ratio of phosphorus(V)-oxide to monohydric alcohol to alkane polyol of 1 to 2 to 4/n, in which n stands for the number of hydroxyl groups present in the alkane polyol molecule, the reaction being effected at approximately 0° to 120° C. with the exclusion of moisture, in the presence of an inert gas, and over a period of approximately 1 to 6 hours; and cooling the resulting reaction product.

The following statements are intended further to illustrate the present process.

As already indicated hereinabove, the acid alkane polyol phosphoric acid esters are important constituents of the mixtures, which are obtained by the present process and which are formed in accordance with the following reaction equation (2)

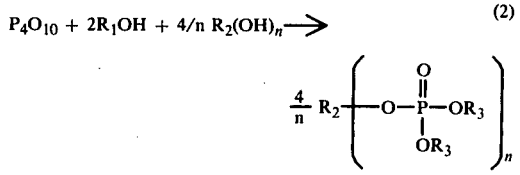

In the above equation (2), $R_1$ stands for an alkyl-, (poly)-alkoxy alkyl or (poly)-alkoxy aryl group, $R_2$ stands for the n-valent radical of an alkane polyol, n stands for the number of hydroxyl groups present per molecule of alkane polyol, $R_3$ stands for hydrogen and/or has the same meaning as $R_1$, $R_1$ and hydrogen being generally used in an average ratio of 1:3.

As it would appear from the fact that the $P_4O_{10}$ molecule undergoes a complexe cleavage reaction comprising six individual reactions, the reaction product identified in the right hand portion of the above equation (2) is only obtained under more or less ideal conditions, as every P-O-P linkage which is subjected to alcoholysis produces a combination of different cleavage products if the other linkage partners of the two phosphorus atoms are distributed asymmetrically, as illustrated in equation (3).

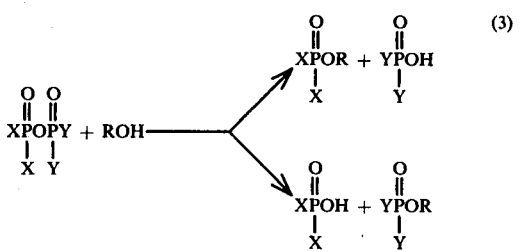

This is the reason why the mixture produced in accordance with equation (1) always contains the identified reaction products together with a certain proportion of unesterified phosphoric acid and phosphoric acid trialkyl esters. By the fact that various alcoholic hydroxyl groups are available for the cleavage reaction in accordance with equation (2), the possibility of effecting further reactions is invariably multiplied. In view of this, in a mixture containing acid phosphoric acid esters, the reaction product defined in equation (2) may be regarded as being only one of its constituents, however one of the type which imparts desirable properties to the mixture.

In carrying out the process of the present invention, use should conveniently be made of devices permitting the reactants to be thoroughly mixed, and heat to be admitted and removed. Useful devices include, for example, vessels of glass, stainless steel or enamelled steel provided with an agitator or circulation pump, feeder for pulverulent solid material, inert gas inlet, heating or cooling jacket, or heating and cooling coil. In those cases in which the starting materials have a solid, pasty or wax-like consistency at the temperatures contemplated, it is possible for them to be mixed together by means of a kneader.

Where it is desirable, it is possible to improve qualitatively the coloration of the products of the present invention by adding phosphorus acid, a dialkyl phosphite or sodium hypophosphite to the blend of monohydric alcohol and alkane polyol, prior to admixing the blend with phosphorus(V)-oxide.

Although the mixtures of the present invention are commonly made without the use of a solvent, it may be advantageous in one case or other to effect the reaction in the presence of an inert solvent (inert with respect to the reactants), i.e. when it is desirable to improve the miscibility of the reactants or to prevent the reaction from taking place too vigorously. After termination of the reaction, the solvent is stripped off from the reaction product at elevated temperature and/or under reduced pressure.

The solvents which may suitably be used comprise, for example: aliphatic or aromatic hydrocarbons, such as cyclohexane, toluene, petroleum ether, chlorinated hydrocarbons or methylene chloride, carbon tetrachloride, 1,2-dichloroethane or diethyl ether. In some cases, it may even be advantageous for the reaction to use as a diluent the alkanol-alkane polyol mixture itself, e.g. in those cases in which the viscosity of the reaction mass containing phosphorus(V)-oxide, which increases with an increasing reaction rate, makes it difficult for it to be stirred. Local overconcentration of phosphorus(V)-oxide may in the end result in undesirable side-reactions which may give rise to more or less undesirable coloration of the reaction product.

While it is basically possible to use any desirable quantity of the alkanol-alkane polyol mixture as a diluent, it is generally sufficient for the unreacted and reacted alkanol-alkanol polyol mixtures to be used in practice in a ratio of 1:0 to 1:1.

The products of the present invention are generally obtained in the form of mean or highly viscous, colorless or slightly colored liquids, or in the form of material having a pasty or wax-like consistency.

Needless to say, the reaction taking place as shown in equation (2) above, produces products which contain various proportions of alkane polyol phosphoric acid esters.

The mixtures of the present invention made from a blend of short chain monohydric alcohols and alkane polyols compare favorably with the acid orthophosphoric acid esters of lower aliphatic alcohols. More specifically, they are of reduced corrosiveness for metals and recommend themselves for use as ingredients of acid cleaning compositions. Products which have longer chain groups attached thereto and which are made by the present process, are suitable for use, after neutralization with the aid of an inorganic or organic base, if desired, as emulsifiers, wetting agents, lubricants or antistatic agents or foam-regulating additives. The halogen-containing products of this invention are interesting intermediates for use in the production of flame-retardant agents.

EXAMPLE 1

333 g (4.5 mols) of n-butanol and 279 g (4.5 mols) of ethylene glycol were placed in a 2-liter glass vessel provided with a stirrer, mixed under nitrogen therein, and the resulting mixture was admixed with 1.8 g of phosphorous acid. Next, 639 g (2.25 mols) of $P_4O_{10}$ was introduced within 110 minutes while the whole was cooled from the outside with the aid of a water-ice mixture. During the introduction period, the temperature of the reaction mixture rose from 22° C. to 55° C. After the exothermal reaction had died down, the mixture was heated within 1 hour to 80° C. and then maintained over 3 hours at 80° to 85° C. The whole was allowed to cool and 1250 g of a viscous colorless liquid containing 51.2 weight % of $P_4O_{10}$ was obtained. The acid number until the first turning point of the titration curve was 331 mg KOH/g at a pH of 4.5, and the total acid number until the second turning point of the titration curve was 564 mg KOH at a pH of 9.5. The product had a density $d_4^{20}$ of 1.438 g/cm$^3$. The dynamic viscosity was 676 poises at 20° C., 65 poises at 50° C. and 21 poises at 80° C. The product was clearly water soluble at concentrations of less than 5 weight % and more than 25 weight %. When used in concentrations lying therebetween, the solution was rendered turbid and, after prolonged stirring, it separated into two phases. The product was also soluble in short chain aliphatic alcohols, e.g. methanol, ethanol and isopropanol.

EXAMPLE 2

The procedure was as in Example 1, but 296.5 g (4 mols) of n-butanol, 425 g (4 mols) of diethylene glycol and 1.8 g of phosphorous acid were reacted with 568 g (2 mols) of $P_4O_{10}$. The reaction gave 1289 g of a very viscous, slightly yellowish product which contained 43.3 weight % of $P_4O_{10}$. The acid number until the first turning point of the titration curve was 341 mg KOH/g at a pH of 4.5 and the total acid number until the second turning point of the titration curve was 506 mg KOH/g at a pH of 9.5. The product was soluble in water at temperatures higher than 85° C. and gave a clear solution. At temperatures lower than 85° C., the solution was rendered turbid. The product was also soluble in isopropanol.

EXAMPLE 3

The procedure was as in Example 1, but 738 g of a product, which was obtained by the additive combination of approximately 4 mols of ethylene oxide with 1 mol of lauryl alcohol with a hydroxyl number of 155 mg KOH/g, 139.5 g (2.25 mols) of ethylene glycol and 2 g of phosphorous acid were reacted with 319 g (1.125 mols) of $P_4O_{10}$ in a stirring vessel of stainless steel. The reaction product was a slightly brownish, highly viscous and gel-like paste, which contained 26.7 weight % of $P_4O_{10}$ and 3.3 weight % of orthophosphoric acid. The product had an acid number until the first turning point of the titration curve of 187 mg KOH/g at a pH of 4.5, and a total acid number until the second turning point of the titration curve of 336 mg KOH/g at a pH of 9.5. The product was soluble in isopropanol, toluene and petroleum ether. In water, it gave a turbid solution.

EXAMPLE 4

208 g (2 mols) of neopentyl glycol, 176 g (2 mols) of commercial grade amyl alcohol (approximately 75% of n-pentanol and 25% of 2-methylbutanol) and 3 g of phosphorous acid were placed in the apparatus described in Example 1, heated to 60° C. and the resulting homogeneous blend was cooled to 40° C. Next, 284 g (1 mol) of $P_4O_{10}$ was introduced within 110 minutes. The temperature rose to 50° C. and was maintained by cooling. After the introduction of $P_4O_{10}$ was terminated, the temperature was increased to 80° C. within 1 hour and the reaction mass was stirred for 2.5 hours at that temperature. Next, the product was allowed to cool down to room temperature. The resulting product had a pasty consistency and contained 43.3 weight % of $P_4O_{10}$. The acid number until the first turning point of the titration curve was 327 mg KOH/g at a pH of 4.5 and the total acid number until the second turning point was 484 mg KOH/g. The product was soluble in short chain aliphatic alcohols, but insoluble in toluene and petroleum ether.

EXAMPLE 5

The procedure was as in Example 1, but 349.5 g of a commercial mixture chiefly of straight chain $C_{16}$-$C_{19}$ alcohols with a hydroxyl number of 211 mg KOH/g, 120.2 g (1.34 mols) of butane-diol-1,2, and 2 g of phosphorous acid were reacted with 189.3 g (0.67 mol) of $P_4O_{10}$. The reaction gave 660 g of a slightly yellowish paste which contained 28.7 weight % of $P_4O_{10}$. It had an acid number until the first turning point of the titration curve of 227 mg KOH/g at a pH of approximately 4.5 and a total acid number until the second turning point of the titration curve of 393 mg KOH/g. The product was soluble in isopropanol, but insoluble in water, toluene and petroleum ether.

EXAMPLE 6

203.3 g (1.67 mols) of thiodiglycol and 123.3 g (1.67 mols) of n-butanol, which were placed in a glass vessel provided with an agitator, thermometer, gas inlet, heating and cooling means, and a closable feeding device, were mixed under nitrogen therein, and the whole was admixed with 2.5 g of phosphorous acid. Next, 238 g (0.835 mol) of $P_4O_{10}$ was added within 50 minutes with agitation and while cooling. The temperature of the reaction mixture rose from 22° C. to 34° C. The material in the vessel was heated within 1 hour to 80° C. and kept at that temperature over a period of 4 hours. The resulting warm product was slightly brownish and highly viscous. After cooling, it was obtained in the form of a plastic mass, which gave an emulsion in warm water. The product was insoluble in isopropanol, petroleum ether and toluene. It contained 42.0 weight % of $P_4O_{10}$ and had an acid number until the first turning point of the titration curve of 317 mg KOH/g at a pH of 4.5. The total acid number until the second turning point of the titration curve was 565 mg KOH/g at a pH of 9.5.

EXAMPLE 7

The procedure was as in Example 1, but 404 g of a product, which was obtained by the additive combination of 6 mols of ethylene oxide with 1 mol of nonyl phenol, 60.8 g of propanediol-1,3 and 1.5 g of phosphorous acid were mixed together and reacted with 113.6 g of phosphorus(V)-oxide, and 548 g of a viscous, clear and slightly yellowish phosphoric acid ester product was obtained. It contained 19.6 weight % of $P_4O_{10}$. The acid number until the first turning point of the titration curve was 145 mg KOH/g at a pH of approximately 4.5, and the total acid number until the second turning point of the titration curve was 240 mg KOH/g at a pH approximately of 9.5. The product was insoluble in water and petroleum ether, but soluble in iso-propanol and toluene.

EXAMPLE 8

262 g (1 mol) of dibromoneopentyl glycol and 1.4 g of phosphorous acid were dissolved while heating to 80° C. in 125 g of 2-bromoethanol (1 mol). The resulting liquid phase was cooled to 45° C. and admixed with 142 g (0.5 mol) of phosphorus(V)-oxide, the mixture being kept at a maximum temperature of 50° C. by cooling with ice-water. The reaction was terminated by heating to 80° C. over a period of two hours. After cooling. a very viscous brownish product which contained 26.9 weight % of $P_4O_{10}$ and 45.2 weight % of bromine was obtained. The product was immiscible with petroleum ether, but soluble in warm water, isopropanol and toluene. On cooling the solutions to room temperature, they commenced separating into phases. The acid number until the first turning point of the titration curve was 217 mg KOH/g at a pH of approximately 4.5, and the total acid number until the second turning point of the titration curve was 321 mg KOH/g at a pH of approximately 9.5.

EXAMPLE 9

178.6 g of a mixture of isomeric alcohols of the formula:

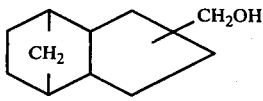

with a hydroxyl number of 312 mg KOH/g, which was obtained by subjecting cyclopentadiene to hydroformylation and hydrogenation, was mixed with 62 g of ethylene glycol and 1.4 g of phosphorous acid, and the resulting mixture was reacted with 142 g of $P_4O_{10}$, in the manner described in Example 1. The reaction product which was highly viscous and scarcely flowable contained 33.2 weight % of $P_4O_{10}$, had an acid number until the first turning point of the titration curve of 262 mg KOH/g at a pH of 4.5, and had a total acid number until the second turning point of 458 mg KOH/g at a pH of approximately 9.5.

EXAMPLE 10

A blend of 136.5 g of a mixture of isomeric diols of the formula

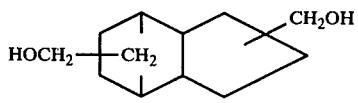

with a hydroxyl number of 165.8 mg KOH/g, which was prepared by subjecting cyclopentadiene to hydroformylation and hydrogenation, 124 g of n-dodecanol and 1 g of phosphorous acid was reacted with 94.7 g of $P_4O_{10}$, in the manner described in Example 1. The resulting highly viscous product contained 25.3 weight % of $P_4O_{10}$, had an acid number until the first turning point of the titration curve of 199 mg KOH/g at a pH of approximately 4.5, and had a total acid number until the second turning point of the titration curve of 312 mg KOH/g at a pH of approximately 9.5.

EXAMPLE 11

135.0 g (2.25 mols) of isopropanol was mixed with 138.2 g of glycerol (1.5 mols) and 3.2 g of phosphorous acid, and the resulting mixture was reacted portionwise with 319.5 g (1.125 mols) of $P_4O_{10}$, the temperature of the reaction mixture being kept at approximately 30° C. by cooling with ice-water. Following the introduction of $P_4O_{10}$, the reaction was completed by heating to 65° C. The resulting colorless viscous reaction product contained 58.9 weight % of $P_4O_{10}$, had an acid number until the first turning point of the titration curve of 419 mg KOH/g at a pH of approximately 4.5, and had a total acid number until the second turning point of 717 mg KOH/g at a pH of approximately 9.5. The product was soluble in water and short chain alcohols.

EXAMPLE 12

429 g of a commercial blend of primary linear alcohols with an even number of C-atoms within the range $C_{20}$ to $C_{24}$ and a hydroxyl number of 142 mg KOH/g was mixed with 99 g of butane diol-1,2 and fused at 65° C. to give a homogeneous liquid phase. After cooling to 50° C., the whole was admixed within 90 minutes with 156.2 g of $P_4O_{10}$, the reaction mass being kept at 50° to 60° C. by cooling. The reaction was terminated by heating to 80° C. over a period of 3 hours. After cooling to room temperature, the ester mixture was obtained in the form of a light brown waxy mass which contained 21.5 weight % of $P_4O_{10}$, had an acid number until the first turning point of the titration curve of 155 mg KOH/g at a pH of approximately 4.5, and had a total acid number until the second turning point of 265 mg KOH/g at a pH of approximately 9.5.

EXAMPLE 13

36.4 g (0.2 mol) of D(−)-mannitol was mixed with 70.8 g (0.6 mol) of butyl glycol and the resulting mixture was reacted over a period of 60 minutes with 85.2 g (0.3 mol) of $P_4O_{10}$, the reaction temperature being kept at 30°–40° C. by cooling with ice water. To complete the reaction with $P_4O_{10}$, the very viscous reaction mass was stirred for 1 hour at 40° C. and for a further 1 hour at 80° C. The resulting very viscous and slightly brownish phosphoric acid ester product contained 44.5 weight % of $P_4O_{10}$, was soluble in water and also soluble in a water-isopropanol mixture in the ratio of 1:3. The acid number until the first turning point of the titration curve was 332 mg KOH/g at a pH of approximately 4.5, and the total acid number until the second turning point was 603 mg KOH/g at a pH of approximately 9.5.

EXAMPLE 14

A mixture of 276.5 g (6 mols) of ethanol and 372.5 g (6 mols) of ethylene glycol was placed in a 2 liter stirring vessel and admixed therein within 140 minutes with 568 g (2 mols) of phosphorus(V)-oxide with vigorous agitation, the mixture being kept at a maximum temperature of 25° C. by cooling. Next, the reaction mixture was gradually heated to 80° C. and stirred for 2 hours at that temperature. After cooling to room temperature, 1180 g of a clear, very slightly colored liquid was obtained. It contained 48.7 weight % of $P_4O_{10}$, had an acid number until the first turning point of the titration curve of 336 mg KOH/g at a pH of approximately 4.5, and had a total acid number until the second turning point of the titration curve of 557 mg KOH/g at a pH of approximately 9.5. The density was 1.446 g/cm$^3$, the dynamic viscosity was 6024 centipoises at 20° C., 765 centipoises at 50° C. and 185 centipoises at 80° C. The product was miscible with water in any desired ratio.

EXAMPLE 15

The procedure was as in Example 14, but 296 g (4 mols) of n-butanol was reacted with 248 g (4 mols) of ethylene glycol and 454 g (1.6 mols) of phosphorus(V)-oxide. 984 g of a clear colorless liquid which contained 46.1 weight % of $P_4O_{10}$, had an acid number until the first turning point of the titration curve of 315 mg KOH/g, and had an acid number until the second turning point of the titration curve of 529 mg KOH/g, was obtained. The density was 1.351 g/cm$^3$, the dynamic viscosity was 9449 centipoises at 20° C., 1135 centipoises at 50° C., and 262 centipoises at 80° C. The product used in concentrations higher than 25 weight % gave clear solutions in water. At lower concentrations, the solutions were rendered turbid.

EXAMPLE 16

Use of product of Example 1 as a bright rinsing agent. 6 smooth beaker-shaped and 6 cup-shaped dringing glasses were placed in a domestic dishwashing machine, washed once, and then rinsed with the use of an aqueous solution of the product of Example 1. The washing operation was effected with the aid of a wash liquour containing 40 g per liter of a cleaning composition composed of:

56 weight % of pentasodium triphosphate
35 weight % of sodium metasilicate
5 weight % of sodium carbonate
2 weight % of sodium dichloroisocyanurate dihydrate, and
2 weight % of a product obtained by the additive combination of 12 mols of ethylene oxide with 1 mol of a $C_{16}$ fatty alcohol.

After this washing operation, the articles were rinsed with an aqueous solution containing a predetermined concentration of the above rinsing agent, and the brightness of the rinsed articles was determined in a non-reflecting black light box, as described by T. Altenschöpfer in "Seifen-öle-Fette-Wachse", 98, No. 24/1972, by counting the number of stains and streaks on the articles. The washing and rinsing operations with the use of a rinsing liquor containing a given predetermined concentration of the rinsing agent was repeated 10 times, and the average number of stains and streaks for the 10 rinsing operations was taken as the final value for the brightness effect. The results obtained are indicated in the Table hereinafter, in column II, which shows that the brightness obtainable is a function of the concentration of the rinsing composition in the rinsing liquour.

EXAMPLE 17 (Comparative Example)

The procedure was as in Example 16, except that monobutyl phosphate was used as a rinsing agent. The results obtained are indicated in the following Table.

TABLE

| Exp. No. | I | II | III |
|---|---|---|---|
| 1 | 5 | 268 | 300 |
| 2 | 10 | 230 | 274 |
| 3 | 20 | 168 | 198 |
| 4 | 30 | 98 | 180 |
| 5 | 40 | 63 | 150 |
| 6 | 50 | 66 | 112 |
| 7 | 60 | 52 | 75 |
| 8 | 70 | 35 | 73 |
| 9 | 80 | 63 | 91 |
| 10 | 90 | 72 | 156 |

TABLE-continued

In the Table:
Column I shows: Concentration of rinsing agent in rinsing liquor (mg/liter)
Column II shows: Number of stains and streaks on articles rinsed with the rinsing agent of Example 16
Column III shows: Number of stains and streaks on articles rinsed with the rinsing agent of Example 17.

The Table shows that the rinsing agent of Example 16, i.e according to the present invention, produces a better brightness effect than the comparative rinsing agent of Example 17, for a given concentration.

I claim:

1. Mixtures of acid phosphoric acid esters, the mixtures having been made by a process wherein $P_4O_{10}$ is reacted by mixing or kneading it with a blend consisting of a monohydric alcohol and an alkane polyol containing 2 to 12 carbon atoms and 2 to 6 hydroxyl groups in a molar ratio of $P_4O_{10}$ to monohydric alcohol to alkane polyol of 1 to 2 to 4/n, n being the number of hydroxyl groups present in the alkane polyol molecule; carrying out the reaction at approximately 0° to 120° C. in the presence of an inert gas and over a period of approximately 1 to 6 hours; and cooling the resulting reaction product.

2. In a process for making a mixture of orthophosphoric acid esters by reacting phosphorus(V)-oxide with a mixture of a monohydric alcohol and a polyhydric alcohol under anhydrous conditions, the improvement which comprises: reacting $P_4O_{10}$ by mixing or kneading it with a blend consisting of a monohydric alcohol and an alkane polyol containing 2 to 12 carbon atoms and 2 to 6 hydroxyl groups in a molar ratio of $P_4O_{10}$ to monohydric alcohol to alkane polyol of 1 to 2 to 4/n, n being the number of hydroxyl groups present in the alkane polyol molecule; carrying out the reaction at approximately 0° to 120° C. in the presence of an inert gas and over a period of approximately 1 to 6 hours; and cooling the resulting reaction product.

3. The process as claimed in claim 2, wherein the monohydric alcohol is an aliphatic alcohol having 1 to 22 carbon atoms or the reaction product of an aliphatic alcohol having 1 to 22 carbon atoms or of a phenol having 6 to 18 carbon atoms with 2 to 20 moles of ethylene oxide.

4. The process as claimed in claim 3, wherein the monohydric alcohol is selected from methanol, ethanol, isopropanol, n-butanol, isobutanol, cyclohexanol, 2-ethylhexanol, lauryl alcohol, isotridecyl alcohol, stearyl alcohol, oleyl alcohol, a commercial mixture of aliphatic alcohols, 2-chloroethanol, 2,3-dibromopropanol-1, 3-methoxybutanol-1 or 2-phenylpropanol.

5. The process as claimed in claim 3, wherein the monohydric alcohol is the product obtained by the additive combination of ethylene oxide with a compound selected from the group consisting of methyl glycol, ethyl glycol, butyl glycol and butyl diglycol, or the product obtained by the additive combination of 4 mols of ethylene oxide with 1 mol of lauryl alcohol, of 8 mols of ethylene oxide with 1 mol of stearyl alcohol, of 6 mols of ethylene oxide with 1 mol of phenol, or of 8 mols of ethylene oxide with 1 mol of nonyl phenol.

6. The process as claimed in claim 2, wherein the alkane polyol is selected from ethylene glycol, propane diol-1,2, propane diol-1,3, butane diol-1,3, butane diol-1,4, diethylene glycol, polyethylene glycol, neopentyl glycol, dibromoneopentyl glycol, glycerol, trimethylol propane, mannitol or pentaerythritol.

7. The process as claimed in claim 2, wherein phosphorus(V)-oxide and monohydric alcohol and alkane diol are used in a molar ratio of 1:2:2.

8. The process as claimed in claim 2, wherein phosphorus(V)-oxide and monohydric alcohol and alkane tetrol are used in a molar ratio of 1:2:1.

9. The process as claimed in claim 2, wherein the phosphorus(V)-oxide is reacted with the monohydric alcohol and the alkane polyol during the strongly exothermal phase of the reaction at 0° to 60° C. by cooling the reaction mixture, and reacted during the end phase of the reaction at 80° to 100° C. by heating the reaction mixture.

10. The process as claimed in claim 9, wherein the reaction is effected at a temperature of 20° to 40° C.

11. The process as claimed in claim 2, wherein the inert gas is nitrogen.

12. The process as claimed in claim 2, wherein the reaction is effected over a period of 1 to 3 hours.

* * * * *